(12) United States Patent
Ikeda et al.

(10) Patent No.: US 8,486,379 B2
(45) Date of Patent: *Jul. 16, 2013

(54) LIP COSMETICS

(75) Inventors: Tomoko Ikeda, Yokohama (JP); Tomo Osawa, Yokohama (JP); Noriko Tomita, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/806,764

(22) PCT Filed: Jun. 7, 2011

(86) PCT No.: PCT/JP2011/063077
§ 371 (c)(1),
(2), (4) Date: Dec. 22, 2012

(87) PCT Pub. No.: WO2012/002117
PCT Pub. Date: Jan. 5, 2012

(65) Prior Publication Data
US 2013/0101539 A1  Apr. 25, 2013

(30) Foreign Application Priority Data
Jun. 29, 2010 (JP) ................. 2010-147387

(51) Int. Cl.
*A61K 8/891* (2006.01)
*A61K 8/31* (2006.01)
*A61K 8/34* (2006.01)
*A61Q 1/04* (2006.01)

(52) U.S. Cl.
USPC ............................................... 424/64

(58) Field of Classification Search
USPC ............................................... 424/64
See application file for complete search history.

(56) References Cited

U.S. PATENT DOCUMENTS

| 5,672,339 A | 9/1997 | Soyama et al. |
| 6,045,782 A | 4/2000 | Krog et al. |
| 6,482,398 B1 | 11/2002 | Rabe et al. |
| 2001/0031269 A1 | 10/2001 | Arnaud |
| 2008/0102048 A1* | 5/2008 | McDermott ............ 424/64 |

FOREIGN PATENT DOCUMENTS

| JP | 57-120508 | 7/1982 |
| JP | 1-233206 | 9/1989 |
| JP | 9-48709 | 2/1997 |
| JP | 2000-053530 | 2/2000 |
| JP | 2001-199846 | 7/2001 |
| JP | 2001-294515 | * 10/2001 |
| JP | 2006-282592 | 10/2006 |
| WO | 96/40044 | 12/1996 |
| WO | 97/16157 | 5/1997 |

OTHER PUBLICATIONS

JP 2001 294515 A, published Oct. 23, 2001, cited in IDS filed Jan. 16, 2013, translation only attached.*
International Preliminary Report on Patentability, Application No. PCT/JP2011/063077, dated Feb. 12, 2013, eight pages.
Patent Abstracts of Japan, Publication No. 2000-053530, Published Feb. 22, 2000, ten pages.
Espacenet bibliographic data for JP 57120508 published Jul. 27, 1982, two pages.
Espacenet bibliographic data for JP 2001294515 published Oct. 23, 2001, two pages.
Espacenet bibliographic data for JP 2006282592 published Oct. 19, 2006, one page.
Espacenet bibliographic data for JP 1233206 published Sep. 19, 1989, two pages.
International Search Report for corresponding PCT/JP2011/063077 mailed Sep. 13, 2011, three pages.

* cited by examiner

*Primary Examiner* — Richard Schnizer
*Assistant Examiner* — Audrea Buckley
(74) *Attorney, Agent, or Firm* — Rankin, Hill & Clark LLP

(57) ABSTRACT

The present invention provides a lip cosmetic that has excellent secondary adhesion resistance effect, good gloss, and excellent stability. The lip cosmetic of the present invention is characterized by comprising the following components (a) to (c):
(a) 4.5 to 35 mass % of isostearyl glyceryl ether;
(b) 20 to 80 mass % of one or more kinds of methyl phenyl silicones that do not separate when mixed with (a) and decamethylcyclopentasiloxane at 90° C. and separate when mixed with (a) and decamethylcyclopentasiloxane at 25° C.;
(c) 4 to 10 mass % of a wax.

6 Claims, No Drawings

LIP COSMETICS

RELATED APPLICATIONS

This application claims the priority of Japanese Patent Application No. 2010-147387 filed on Jun. 29, 2010, which is incorporated herein by reference.

FIELD OF THE INVENTION

The present invention relates to a lip cosmetic, and in particular, relates to a lip cosmetic having excellent secondary adhesion resistance and excellent gloss durability.

BACKGROUND OF THE INVENTION

Conventional lip cosmetic have presented the problem of secondary adhesion, namely a lipstick is transferred onto a site contacted by a lip (for example, a cup) after the lipstick is applied to the lip. By contrast, lipstick compositions having so-called secondary adhesion resistance effect that causes little secondary adhesion have been developed.

For example, Patent Document 1 discloses a transfer-resistant cosmetic composition comprising: a volatile hydrocarbon solvent; a non-volatile silicone compound that can be dissolved or dispersed in the volatile hydrocarbon solvent; and non-volatile hydrocarbon oil that is dissolved in the volatile solvent and is incompatible with the non-volatile silicone compound, wherein the non-volatile hydrocarbon oil has a certain solubility parameter.

However, this transfer-resistant cosmetic composition has room for improvement in stability. Due to its large amount of wax, the feeling in use in a liquid state cannot be obtained, and also gloss is insufficient.

Patent Document 2 discloses a lipstick composition having transfer resistance, comprising perfluoropolyether-type non-volatile oil and volatile oil, which are incompatible with each other. In this Patent Literature 2, oils are separated during application to a support to move onto a first composition.

However, the first composition is in a solid state due to a considerable amount of wax. Thus, a sufficient gloss or moisture cannot be obtained. Moreover, for this system, the incompatible oil phases are difficult to favorably disperse, resulting in the problem of stability against sweating etc.

Patent Document 3 discloses a stick cosmetic having transfer resistance, comprising volatile oil and a silicone surfactant, wherein pigments are favorably dispersed.

However, this stick cosmetic has a large proportion of the volatile oil in the composition and thus has the disadvantage that its matte finish tends to provide a feeling of dryness on lips.

Patent Document 4 discloses a one-phase composition for lipsticks, comprising volatile oil and a silicone resin.

However, after evaporation of the volatile oil, this composition for lipsticks tends to cause a feeling of dryness over time, although it has improved transfer resistance. Moreover, a film of the resin remains on lips. The composition further has the following disadvantages that; it causes a filmy feeling and tightness, and the obtained adhesion is matte.

Patent Document 5 discloses an oil-in-oil emulsion composition comprising: continuous-phase oil comprising a silicone coating agent, volatile silicone oil, non-volatile silicone liquid oil, and an emulsifying agent; and dispersion-phase oil comprising ester oil and a coloring material, wherein the blending quantities of the continuous-phase oil and the dispersion-phase oil are at a dispersion-phase oil/(dispersion-phase oil and continuous-phase oil) ratio of 0.05 to 0.5.

However, this oil-in-oil emulsion composition tends to generate color unevenness due to the presence of the coloring material in the dispersion phase. Furthermore, for this system, temporal stability may be difficult to maintain.

Patent literature 1: Japanese unexamined patent publication No. 2001-199846
Patent literature 2: International unexamined patent publication No. 96/40044
Patent literature 3: International unexamined patent publication No. 97/16157
Patent literature 4: Japanese unexamined patent publication No. H9-48709
Patent literature 5: Japanese unexamined patent publication No. 2000-53530

DISCLOSURE OF THE INVENTION

Problem to be Solved by the Invention

The present invention was made in view of the above-described conventional art. An object of the invention is to provide a lip cosmetic that has excellent secondary adhesion resistance effect, excellent gloss durability after application, and excellent stability.

Means to Solve the Problem

The present inventors have diligently studied; as a result, the present inventors have found that a stable lip cosmetic having, after application, both secondary adhesion resistance and a gloss can be obtained by using a combination of a specific surfactant and a specific oil.

That is, the lip cosmetic of the present invention is characterized by comprising the following components (a) to (c):
(a) 4.5 to 35 mass % of isostearyl glyceryl ether;
(b) 20 to 80 mass % of one or more kinds of methyl phenyl silicones that do not separate when mixed with (a) and decamethylcyclopentasiloxane at 90° C. and separate when mixed with (a) and decamethylcyclopentasiloxane at 25° C.;
(c) 4 to 10 mass % of a wax.

In the lip cosmetic, it is preferable that component (b) contains trimethyl pentaphenyl trisiloxane.

In the lip cosmetic, it is preferable that trimethyl pentaphenyl trisiloxane is 50 mass % or more of the total amount of the component (b).

In the lip cosmetic, it is preferable that (d) water and/or glycerin is additionally blended and the component (d) is 5 mass % or more with respect to the component (a) and 24 mass % or less of the total amount of the cosmetic.

The selection method of (b) methyl phenyl silicone(s) of the present invention is a selection method of (b) 20 to 80 mass % of methyl phenyl silicone(s), which is blended in a lip cosmetic comprising (a) 4.5 to 35 mass % of isostearyl glyceryl ether and (c) 4 to 10 mass % of wax, and the selection method is characterized in that when a 1:1 (mass ratio) mixture of (a) and decamethylcyclopentasiloxane is mixed with (b) at a ratio of 1:2 (mass ratio), the component(s) (b) is methyl phenyl silicone(s) that does not separate at 90° C. and separates at 25° C.

Effect of the Invention

A lip cosmetic having excellent secondary adhesion resistance effect, excellent gloss, and good stability, while maintaining post-application secondary adhesion resistance effect, can be obtained by blending the specific amounts of (a)

isostearyl glyceryl ether, (b) one or more kinds of methyl phenyl silicones that do not separate when mixed with (a) and decamethylcyclopentasiloxane at 90° C. and separate when mixed with (a) at 25° C., and (c) a wax.

BEST MODE FOR CARRYING OUT THE INVENTION

Generally, if the secondary adhesion resistance effect is high, the gloss upon application has a tendency to be lacking. On the other hand, the base having a gloss has a drawback in that the secondary adhesion easily takes place because there is plenty residual oil. In the present invention, by blending a specific surfactant and non-compatible silicone oil therewith, the silicone oil separates into the surface layer, and a gloss is provided. Because the surfactant, in the inner layer, holds in the coloring material, the secondary adhesion is difficult to take place. As a result, a lip cosmetic without secondary adhesion and with an excellent gloss can be obtained.

In the following, each component is described in detail.
((a) Isostearyl Glyceryl Ether)

Isostearyl glyceryl ether, which is component (a) used in the present invention, is preferably monoisostearyl glyceryl ether and can be obtained by various known synthesis methods. It is available as "PENETOL GE-IS (manufactured by Kao Corporation, trade name)".

It is necessary that the blending quantity of component (a) in the present invention is 4.5 to 35 mass % of the total amount of the cosmetic. The blending quantity is preferably 7 to 30 mass %. If the blending quantity of component (a) is too small or too large, the secondary adhesion resistance effect may be inferior. Also, if it is too large, there is a trend that stickiness appears after application.

((b) Methyl Phenyl Silicone)

Methyl phenyl silicone, which is component (b) used in the present invention, will separate from component (a), after application, and form the surface layer; thus the secondary adhesion resistance effect is achieved and the gloss is improved.

In the present invention, component (b) is one or more kinds of methyl phenyl silicones that do not separate when mixed with (a) and decamethylcyclopentasiloxane at 90° C. and separate when mixed with (a) and decamethylcyclopentasiloxane at 25° C., and the methyl phenyl silicone can be one kind or a mixture of two or more kinds.

Here, the presence or absence of "separation" was measured under the following conditions.
(Measurement Condition)

A mixture of (a) and decamethylcyclopentasiloxane (1:1 mass ratio) was prepared. This mixture was used in the ratio (mixture:(b)=1:2 (mass ratio)) and mixed with stirring at 90° C. The mixture was allowed to stand at room temperature (25° C.). When the boundary was uniformly separated into two layers, it was denoted "separated". When it was a cloudy state or a translucent state with a non-uniform boundary or a transparently miscible state without a boundary, it was denoted "not separated".

When two kinds or more of methyl phenyl silicones are used as the component (b), the presence or absence of separation depends upon their blending ratio. Therefore, it is necessary to check the presence or absence of separation in light of the blending ratio of the component (b).

Trimethyl pentaphenyl trisiloxane and diphenyl dimethicone are preferable as the methyl phenyl silicones used in the present invention. It is especially preferable that trimethyl pentaphenyl trisiloxane is contained.

These methyl phenyl silicones can be blended in a ratio so that the component (b) as a whole satisfies the described separation condition.

It is more preferable that trimethyl pentaphenyl trisiloxane is 50 mass % or more of the total amount of the component (b). If the ratio of trimethyl pentaphenyl trisiloxane is low, the separation condition may not be satisfied and the sufficient secondary adhesion resistance effect may not be achieved.

As a commercial trimethyl pentaphenyl trisiloxane, methyl phenyl silicone FZ3156 (165 mm$^2$/s (25° C.), manufactured by Dow Corning Toray Co., Ltd.) can be listed. As a commercial diphenyl dimethicone, silicone KF54 (400 mm$^2$/s (25° C.), manufactured by Shin-Etsu Chemical Co., Ltd.), silicone KF50-300CS (manufactured by Shin-Etsu Chemical Co., Ltd.), silicone KF-54HV (manufactured by Shin-Etsu Chemical Co., Ltd.), and the like can be listed.

As the components (b) of the present invention, as well as the above, diphenylsiloxyphenyl trimethicone (for example, silicone KF56 (14 mm$^2$/s (25° C.), manufactured by Shin-Etsu Chemical Co., Ltd.), phenyl trimethicone (for example, silicone SH556 (22 mm$^2$/s (25° C.), manufactured by Dow Corning Toray Co., Ltd.), and the like can be used.

In particular, when diphenylsiloxyphenyl trimethicone is used, there is an effect in that the gloss improves upon application.

It is necessary that the blending quantity of component (b) is 20 to 80 mass % of the total amount of the cosmetic. The blending quantity is preferably 30 to 80 mass % and more preferably 45 to 70 mass %. If the blending quantity of component (b) is less than 20 mass %, the secondary adhesion easily takes place and there is a little gross. If it exceeds 80 mass %, the secondary adhesion resistance effect is poor.

In the present invention, an oil component other than component (b) can also be blended.

As an optional oil component, it is especially preferable to blend a volatile oil. As volatile oils, volatile hydrocarbon oils, volatile silicone oils, and the like can be listed.

For example, it is preferable that decamethylcyclopentasiloxane is blended and the blending quantity is 0.5 to 25 mass % of the total amount of the cosmetic. By blending decamethylcyclopentasiloxane, the stability is further improved.

((c) Wax)

Wax used in the present invention is not limited in particular as long as it can be normally blended for cosmetics. For example, carnauba wax, candelilla wax, beeswax, ceresin, microcrystalline wax, solid paraffin, Japan wax, and the like can be listed.

It is necessary that the blending quantity of (c) wax is 4 to 10 mass % of the total amount of the cosmetic. The blending quantity is preferably 6 to 9 mass %. If the blending quantity of component (c) is less than 4 mass %, the solidification is difficult. If it exceeds 10 mass %, the spreadability becomes heavy and the gloss is lost.

((d) Water and/or Glycerin)

In the present invention, liquid crystals are formed more easily and the secondary adhesion resistance effect is further improved by additionally blending (d) water and/or glycerin.

The blending quantity of (d) water and/or glycerin is preferably 5 mass % or more and especially preferably 20 mass % or more with respect to the component (a), and preferably 24 mass % or less and especially preferably 18 mass % or less of the total amount of the cosmetic.

In the lip cosmetic of the present invention, in addition to the above-described components, the components normally used in lip cosmetics (for example, oil other than the above-described oils, powder, polymer compound, moisturizer, perfume, antioxidant agent, preservative, beauty component, and the like) can be blended so far as the effect of the present invention is not undermined.

As the moisturizers, for example, polyol moisturizers such as glycerin, propylene glycol, and 1,3-butylene glycol can be listed.

In the present invention, it is preferable to blend a coloring material.

Such coloring materials can be powdery or lake-like (oil-containing state) so far as they are coloring materials normally used in lip cosmetics. They can be inorganic pigments, organic pigments, or pearlescent agents. At the time of the application of the lip cosmetic, the coloring material is held in component (a) and it is present in the inner side of component (b); thus the secondary adhesion is difficult to take place.

The blending quantity of the coloring material is preferably 1 to 13 mass % and especially preferably 3 to 8 mass % of the total amount of the cosmetic.

A film-forming agent can be additionally blended in the lip cosmetic of the present invention.

Examples of film-forming agents include (alkyl acrylate/dimethicone) copolymer and the like. Specifically, Silicone KP545 (manufactured by Shin-Etsu Chemical Co., Ltd.) is commercially available.

The blending quantity of the film-forming agent is preferably 2 to 15 mass % and especially preferably 5 to 10 mass % of the total amount of the cosmetic.

It is preferable that the lip cosmetic of the present invention is constituted so that the separation does not take place throughout the entire production process and the state of one homogeneous phase is maintained. More specifically, it is preferable that the lip cosmetic is constituted so that the entire composition does not separate at 90° C. and the state of one homogeneous phase is maintained.

The lip cosmetic of the present invention can be applied to lipsticks, lip glosses, lip bases, overcoats for lipsticks, lip creams, and the like. The lip cosmetic of the present invention is preferably used as lip solid cosmetics such as a lipstick.

EXAMPLES

The present invention will be further described in the following examples. However, the invention is not limited by these examples. Unless otherwise specified, the blending quantity of each component will be expressed in mass %.

Prior to illustrating the examples, the methods for the effect tests used in the present invention will be explained.

Evaluation (1): Evaluation Test of the Separation State of the (a) and Decamethylcyclopentasiloxane and the Component (b)

The separation state of (b) methyl phenyl silicones was measured under the following conditions. If the separation did not take place at 90° C. and the separation took place at 25° C., it was denoted "A" and others were denoted "C".

(Measurement Condition)

A mixture of (a) and decamethylcyclopentasiloxane (1:1 mass ratio) was prepared. This mixture was used in the ratio (mixture:(b)=1:2 (mass ratio)) and mixed with stirring at 90° C. The mixture was allowed to stand at room temperature (25° C.). When the boundary was uniformly separated into two layers, it was denoted "separated". When it was a cloudy state or a translucent state with a non-uniform boundary or a transparently miscible state without a boundary, it was denoted "not separated".

Evaluation (2): Evaluation Test of the Secondary Adhesion Resistance Effect

The actual usability test by 10 professional panelists was carried out. The five-level sensory evaluation (scoring) of the secondary adhesion resistance effect upon application to the lip was based on the below-described scoring criteria. The determination was by the score average value based on the below-described evaluation criteria.

(Score)
5 points: very excellent
4 points: excellent
3 points: ordinary
2 points: poor
1 point: very poor (Evaluation Criteria)
S: The score average value is 4.5 points or higher and less than 5.0 points.
A*: The score average value is 4.0 points or higher and less than 4.5 points.
A: The score average value is 3.5 points or higher and less than 4.0 points.
B: The score average value is 2.5 points or higher and less than 3.5 points.
C: The score average value is 1.0 point or higher and less than 2.5 points.

The examples listed with "-" in the table had poor stability, and the secondary adhesion resistance effect could not be measured.

Evaluation (3): Evaluation Test of the Stability

The wax uniformity of the cutting plane of the stick-shaped sample was evaluated based on the below-described evaluation criteria.

(Evaluation Criteria)
A*: uniform
A: slightly uniform
B: slightly non-uniform
C: non-uniform The present inventor prepared respective lipsticks with the formulations shown in the below-described Tables 1 to 5 by the ordinary method. The lipsticks were evaluated for the secondary adhesion resistance effect and stability based on the above evaluation criteria. The results are shown in Tables 1 to 5.

In the test examples in Tables 3 to 5 below, the evaluation (1) was carried out; all of them were "A".

TABLE 1

| | Test Example | 1-1 | 1-2 | 1-3 | 1-4 |
|---|---|---|---|---|---|
| (a) | Isostearyl glyceryl ether※1 | 14 | 14 | 14 | 14 |
| (b) | Trimethyl pentaphenyl trisiloxane※2 | 71 | — | — | 40 |
| | Diphenyl dimethicone ※3 | — | 71 | — | 31 |
| | Diphenylsiloxy phenyl trimethicone※4 | — | — | 71 | — |
| (c) | Polyethylene wax | 7 | 7 | 7 | 7 |
| (d) | Water | 3 | 3 | 3 | 3 |
| | Dynamite glycerin | 1 | 1 | 1 | 1 |
| | Coloring material | 4 | 4 | 4 | 4 |
| Evaluation (1): Separation state of the (a) and decamethylcyclopentasiloxane and the component (b) | | A | C | C | A |
| Evaluation (2): Secondary adhesion resistance effect | | A* | — | C | A* |
| Evaluation (3): Stability | | A | C | A | A |

※1: PENETOL GE-IS (manufactured by Kao Corporation)
※2: Methyl phenyl silicone FZ3156 (manufactured by Dow Corning Toray Co., Ltd.)
※3: Silicone KF54 (manufactured by Shin-Etsu Chemical Co., Ltd.)
※4: Silicone KF56 (manufactured by Shin-Etsu Chemical Co., Ltd.)

As seen from Table 1, in the samples of Test Example 1-1 and Test Example 1-4, which comprise isostearyl glyceryl ether, various methyl phenyl silicones, and wax and satisfy the separation condition of the evaluation (1), the secondary adhesion resistance effect and the stability were excellent.

On the other hand, in the samples of Test Example 1-2 and Test Example 1-3, which comprise different kinds or a different blending ratio of methyl phenyl silicones from those of Test Example 1-1 and Test Example 1-4 and do not satisfy the separation condition of evaluation (1), the secondary adhesion resistance effect was poor or the stability was poor.

TABLE 2

| Test Example | | 1-1 | 2-1 | 2-2 | 1-4 | 2-3 | 2-4 | 2-5 | 1-2 |
|---|---|---|---|---|---|---|---|---|---|
| (a) | Isostearyl glyceryl ether·X·1 | 14 | 14 | 14 | 14 | 14 | 14 | 14 | 14 |
| (b) | Trimethyl pentaphenyl trisiloxane·X·2 | 71 | 60 | 50 | 40 | 30 | 20 | 10 | — |
| | Diphenyl dimethicone·X·3 | — | 11 | 21 | 31 | 41 | 51 | 61 | 71 |
| (c) | Polyethylene wax | 7 | 7 | 7 | 7 | 7 | 7 | 7 | 7 |
| | Water | 3 | 3 | 3 | 3 | 3 | 3 | 3 | 3 |
| (d) | Dynamite glycerin | 1 | 1 | 1 | 1 | 1 | 1 | 1 | 1 |
| | Coloring material | 4 | 4 | 4 | 4 | 4 | 4 | 4 | 4 |
| Evaluation (1): Separation state of the (a) and decamethylcyclopentasiloxane and the component (b) | | A | A | A | A | C | C | C | C |
| Evaluation (2): Secondary adhesion resistance effect | | A* | A* | A* | A* | — | — | — | — |
| Evaluation (3): Stability | | A | A | A | A | C | C | C | C |

As seen from Table 2, it was clarified that in the lip cosmetic wherein isostearyl glyceryl ether, methyl phenyl silicones (trimethyl pentaphenyl trisiloxane and/or diphenyl dimethicone), and wax were blended, the separation state varied depending upon the blending ratio of various methyl phenyl silicones; thus the secondary adhesion resistance effect and the stability were influenced. It is seen that the selection method of methyl phenyl silicones is a very important matter to achieve the effect of the present invention.

Thus, it is necessary that the lip cosmetic of the present invention comprises (a) isostearyl glyceryl ether, (b) methyl phenyl silicone, and (c) a wax. And it is also necessary that the methyl phenyl silicone does not separate at 90° C. and separates at 25° C. when a mixture of (a) and decamethylcyclopentasiloxane (1:1 mass ratio) and components (b) are mixed (mixture:(b)=1:2 (mass ratio)).

TABLE 3

| Test Example | | 1-1 | 3-1 | 3-2 |
|---|---|---|---|---|
| (a) | Isostearyl glyceryl ether·X·1 | 14 | 30 | 2 |
| (b) | Trimethyl pentaphenyl trisiloxane·X·2 | 71 | 35.8 | 71.4 |
| | Decamethylcyclopentasiloxane | — | 15 | 15 |
| (c) | Polyethylene wax | 7 | 7 | 7 |
| (d) | Water | 3 | 6.3 | 0.5 |
| | Dynamite glycerin | 1 | 1.9 | 0.1 |
| | Coloring material | 4 | 4 | 4 |
| Evaluation (2): Secondary adhesion resistance effect | | A* | A | C |
| Evaluation (3): Stability | | A | A | A |

As seen from Table 3, the secondary adhesion resistance effect is influenced by the blending quantity of (a) isostearyl glyceryl ether in the lip cosmetic.

As a result of the further investigations by the present inventors, it was clarified that the blending quantity of (a) isostearyl glyceryl ether is 4.5 to 35 mass % of the total amount of cosmetics.

TABLE 4

| Test Example | | 4-1 | 1-1 | 4-2 | 4-3 |
|---|---|---|---|---|---|
| (a) | Isostearyl glyceryl ether·X·1 | 6 | 14 | 14 | 14 |
| (b) | Trimethyl pentaphenyl trisiloxane·X·2 | 82 | 71 | 25 | 18 |
| | Decamethylcyclopentasiloxane | — | — | 46 | 53 |
| (c) | Polyethylene wax | 4 | 7 | 7 | 7 |
| (d) | Water | 3 | 3 | 3 | 3 |
| | Dynamite glycerin | 1 | 1 | 1 | 1 |
| | Coloring material | 4 | 4 | 4 | 4 |
| Evaluation (2): Secondary adhesion resistance effect | | C | A* | B | C |
| Evaluation (3): Stability | | A | A | A | A |

As seen from Table 4, the secondary adhesion resistance effect is influenced by the blending quantity of (b) methyl phenyl silicones in the lip cosmetic.

Accordingly, it is necessary that the blending quantity of (b) methyl phenyl silicones is 20 to 80 mass % of the total amount of the cosmetics.

TABLE 5

| Test Example | | 5-1 | 5-2 | 5-3 | 5-4 |
|---|---|---|---|---|---|
| (a) | Isostearyl glyceryl ether·X·1 | 14 | 14 | 14 | 14 |
| (b) | Trimethyl pentaphenyl trisiloxane·X·2 | 56 | 40 | 56 | 56 |
| | Decamethylcyclopentasiloxane | 19 | 11 | 15 | 15 |
| (c) | Polyethylene wax | 7 | 7 | 7 | 7 |
| (d) | Water | — | 18 | 4 | — |
| | Dynamite glycerin | — | 6 | — | 4 |
| | Coloring material | 4 | 4 | 4 | 4 |
| Evaluation (2): Secondary adhesion resistance effect | | A* | A* | A* | A* |
| Evaluation (3): Stability | | A | A | A | A |

As seen from Table 5, in the samples of Test Examples 5-2 to 5-4, wherein a part of the sample of Test Example 5-1, which contains the suitable components (a) to (c), was replaced with water and/or glycerin, the secondary adhesion resistance effect and the stability were excellent as were the case for Test Example 5-1, and the secondary adhesion resistance effect was especially excellent compared with the sample of Test Example 5-1.

Accordingly, it is preferable that (d) water and/or glycerin is contained in the lip cosmetic of the present invention.

Hereinafter, formulation examples of the lip cosmetic of the present invention will be illustrated. It is to be understood that the present invention is not limited by these formulation examples and is specified by the scope of claims.

Formulation Example 1

| Blending compounds | mass % |
|---|---|
| (1) Isostearyl glyceryl ether | 14 |
| (2) Trimethyl pentaphenyl trisiloxane (Methyl phenyl silicone FZ3156 (manufactured by Dow Corning Toray Co., Ltd.)) | 71 |
| (3) Coloring material | 7 |
| (4) Polyethylene wax | 4 |
| (5) Ion-exchanged water | 3 |
| (6) Glycerin | 1 |

Production Method:

Components (1) to (4) were mixed at 90° C., and warmed components (5) and (6) were added and mixed. The deaeration and filling were carried out and then it was cooled.

Formulation Example 2

| Blending compounds | mass % |
|---|---|
| (1) Isostearyl glyceryl ether | 14 |
| (2) Trimethyl pentaphenyl trisiloxane (Methyl phenyl silicone FZ3156 (manufactured by Dow Corning Toray Co., Ltd.)) | 48 |
| (3) (Alkyl acrylate/dimethicone) copolymer | 5 |
| (4) Decamethylcyclopentasiloxane | 11 |
| (5) Polyethylene wax | 9 |
| (6) Coloring material | 5 |
| (7) Ion-exchanged water | 6 |
| (8) Glycerin | 2 |

Production Method:

Components (1) to (6) were mixed at 90° C., and warmed components (7) and (8) were added and mixed. The deaeration and filling were carried out and then it was cooled.

Formulation Example 3

| Blending compounds | mass % |
|---|---|
| (1) Isostearyl glyceryl ether | 14 |
| (2) Trimethyl pentaphenyl trisiloxane (Methyl phenyl silicone FZ3156 (manufactured by Dow Corning Toray Co., Ltd.)) | 29 |
| (3) Dimethyl diphenyl polysiloxane (Silicone KF54 (manufactured by Shin-Etsu Chemical Co., Ltd.)) | 20 |
| (4) Stearoyl inulin | 1 |
| (5) Decamethylcyclopentasiloxane | 15 |
| (6) Polyethylene wax | 8 |
| (7) Coloring material | 5 |
| (8) Ion-exchanged water | 6 |
| (9) Glycerin | 2 |

Production Method:

Components (1) to (7) were mixed at 90° C., and warmed components (8) and (9) were added and mixed. The deaeration and filling were carried out and then it was cooled.

What is claimed is:

1. A lip cosmetic composition comprising the following components (a) to (c): (a) 4.5 to 35 mass % of isostearyl glyceryl ether; (b) 20 to 80 mass % of one or more kinds of methyl phenyl silicones that do not separate when mixed with (a) and decamethylcyclopentasiloxane at 90° C. and separate when mixed with (a) and decamethylcyclopentasiloxane at 25° C., wherein the methyl phenyl silicone(s) is selected from trimethyl pentaphenyl trisiloxane, diphenyl dimethicone, diphenylsiloxy phenyl trimethicone, and phenyl trimethicone; (c) 4 to 10 mass % of a wax.

2. The lip cosmetic composition according to claim 1, wherein component (b) contains trimethyl pentaphenyl trisiloxane.

3. The lip cosmetic composition according to claim 2, wherein trimethyl pentaphenyl trisiloxane is 50 mass % or more of the total amount of component (b).

4. The lip cosmetic composition according to claim 3, wherein the composition further comprises (d) water and/or glycerin and wherein the component (d) is 5 mass % or more of component (a) and 24 mass % or less of the cosmetic composition.

5. The lip cosmetic composition according to claim 1, wherein the composition further comprises (d) water and/or glycerin and wherein the component (d) is 5 mass % or more of component (a) and 24 mass % or less of the cosmetic composition.

6. The lip cosmetic composition according to claim 2, wherein the composition further comprises (d) water and/or glycerin and wherein the component (d) is 5 mass % or more of component (a) and 24 mass % or less of the cosmetic composition.

* * * * *